United States Patent [19]

Nakasugi

[11] Patent Number: 5,064,957

[45] Date of Patent: Nov. 12, 1991

[54] NOVEL AMINE COMPOUND AND METHOD FOR THE PREPARATION THEREOF

[75] Inventor: Nobuyasu Nakasugi, Kyoto, Japan

[73] Assignee: San-Apro Limited, Kyoto, Japan

[21] Appl. No.: 492,937

[22] Filed: Mar. 13, 1990

[30] Foreign Application Priority Data

Mar. 16, 1989 [JP] Japan ................................ 1-64581

[51] Int. Cl.$^5$ .......................................... C07D 295/12
[52] U.S. Cl. ...................................... 544/86; 528/53; 521/115
[58] Field of Search ......................................... 544/86

[56] References Cited

U.S. PATENT DOCUMENTS 4,379,861  4/1983  Haas et al. ............................ 528/53

*Primary Examiner*—C. Warren Ivy
*Assistant Examiner*—Celia Chang
*Attorney, Agent, or Firm*—Wyatt, Gerber, Burke and Badie

[57] ABSTRACT

A novel morpholino-substituted tertiary amine compound is proposed which is tris[2-(4-morpholino)ethyl] amine or a derivative thereof by optionally substituting methyl and/or ethyl groups for a part or all of the hydrogen atoms at the 2- and 6-positions of the morpholine rings. The amine compound can be synthesized by heating tris[N,N-di(2-hydroxyethyl)aminoethyl] amine or a corresponding derivative thereof in a mixture with sulfuric acid. The amine compound is useful as a catalyst for the urethane-forming reaction between a polyisocyanate compound and a polyol compound without the problems of environmental pollution or unpleasant odor as in the use of methyl or ethyl morpholine for the same purpose.

3 Claims, 4 Drawing Sheets

FIG. I

NOVEL AMINE COMPOUND AND METHOD FOR THE PREPARATION THEREOF

BACKGROUND OF THE INVENTION

The present invention relates to a novel amine compound and a method for the preparation thereof. More particularly, the invention relates to a novel tertiary amine compound having morpholino-substituted ethyl groups and useful as a catalyst for the urethane-forming reaction between a polyisocyanate compound and a polyol compound as well as a method for the synthetic preparation of such an amine compound. The invention also relates to a method for the preparation of a polyurethane by using the novel amine compound as a catalyst.

It is an established technology to use methyl morpholine or ethyl morpholine as a catalyst for the urethane-forming reaction between a polyisocyanate compound and a polyol compound. These morpholine compounds, however, are, despite their excellent catalytic performance, not quite satisfactory as a catalyst for the urethane-forming reaction since these compounds have a relatively low boiling point and have an intense malodor to cause a serious problem of pollution in the working environment. Therefore, it is eagerly desired to develop a novel amine compound free from these problems and disadvantages and capable of exhibiting excellent catalytic performance for the urethane-forming reaction like methyl and ethyl morpholines.

SUMMARY OF THE INVENTION

Accordingly, the inventor has continued extensive investigations to discover an amine compound which meets the above mentioned requirements including synthesis of various kinds of novel amine compounds and has arrived at a discovery that a tertiary amine compound having specific morpholino-subnstituted ethyl groups is very promising as the catalyst for the urethane-forming reaction without the problems and disadvantages in methyl and ethyl morpholines.

Thus, the novel tertiary amine compound of the invention, which is not known in the prior art and has not been described in any literature and can be in the form of a free amine or in the form of a salt, is a tertiary amine compound represented by the general formula

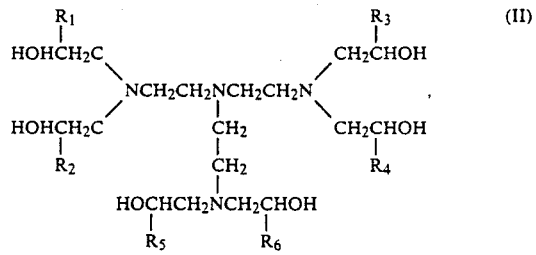

in which $R_1$, $R_2$, $R_3$, $R_4$, $R_5$ and $R_6$, each independently from the others, are a hydrogen atom, methyl group or ethyl group.

The above defined novel amine compound can be prepared by heating an alkanol amine compound represented by the general formula

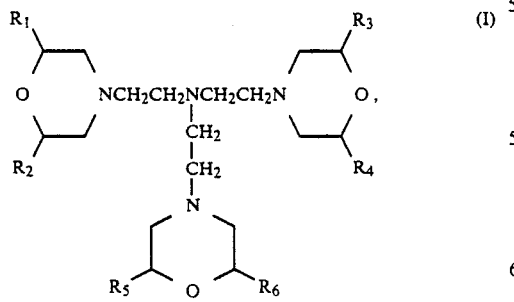

in which $R_1$, $R_2$, $R_3$, $R_4$, $R_5$ and $R_6$ each have the same meaning as defined above, as a mixture with sulfuric acid.

The above described amine compound or a salt thereof is useful as a principal ingredient in the catalyst for the urethane-forming reaction. Thus, a polyurethane resin, either unfoamed or foamed, can be prepared by the reaction of a polyisocyanate compound and a multifunctional active hydrogen-containing compound, e.g., polyol compounds, in the presence of the inventive amine compound or a salt thereof, if necessary, together with a cocatalyst, blowing agent and other optional additives.

DETAILED DESCRIPTION OF THE PREFERRED EMBODIMENTS

Figure 1:
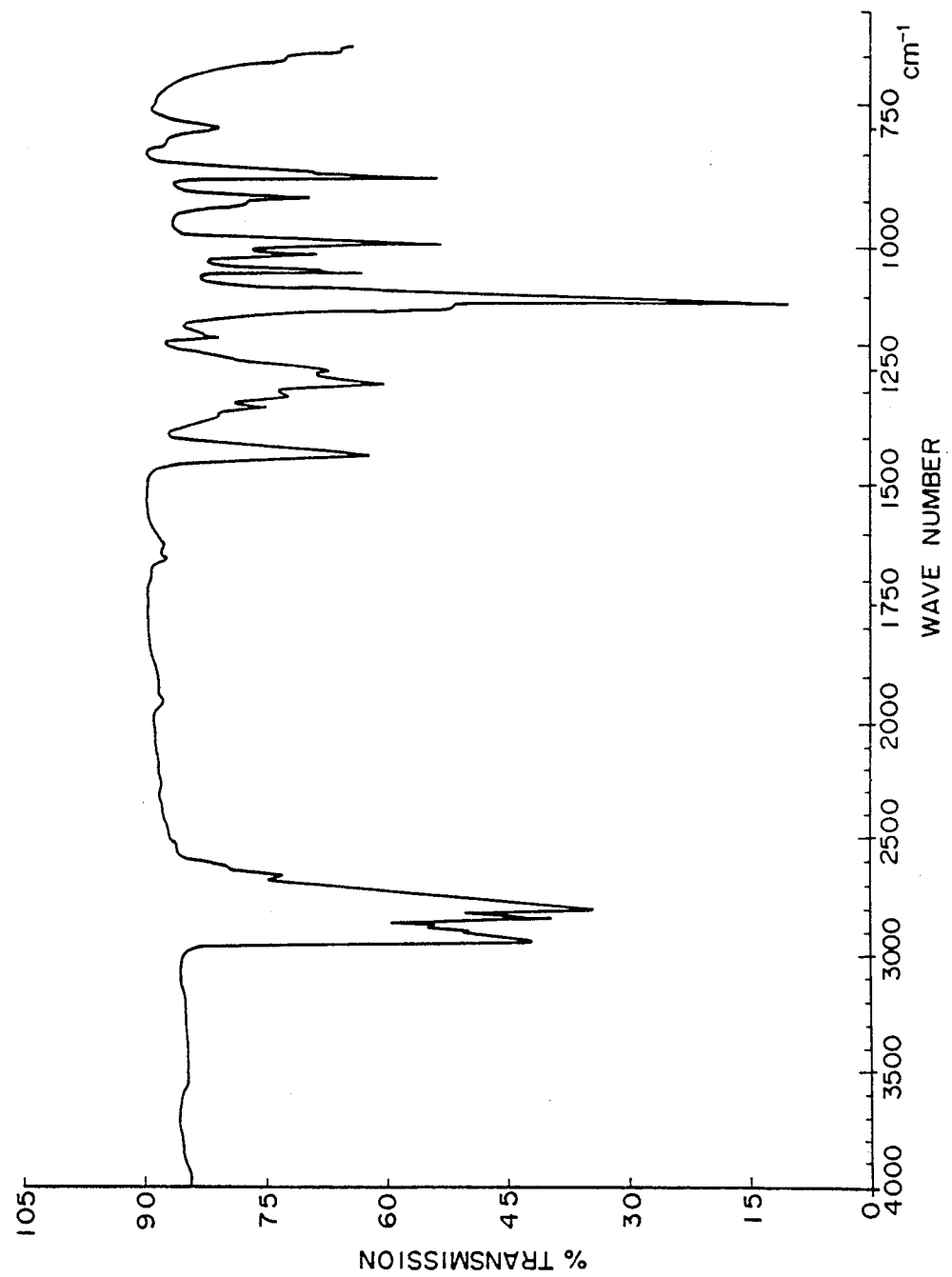
FIGS. 1 and 2 show an infrared absorption spectrum and a nuclear magnetic resonance absorption spectrum, respectively, of the inventive amine compound synthesized in Example 1.

As is described above, the novel amine compound of the invention is a tertiary amine compound represented by the above given general formula (I) having three morpholino-substituted ethyl groups. In the general formula (I), the groups denoted by the symbols $R_1$, $R_2$, $R_3$, $R_4$, $R_5$ and $R_6$ are each, independently from the others, a hydrogen atom, methyl group or ethyl group. Preferably, these groups are each selected from a hydrogen atom and a methyl group.

The above defined amine compound of the invention has a much larger molecular weight than methyl or ethyl morpholine and the boiling point thereof is also much higher than those of methyl and ethyl morpholines with extremely low volatilizability and almost free from any unpleasant odor despite the quite high activity as a catalyst for. the urethane-forming reaction. Accordingly, no problems of pollution in the working environments are caused when the inventive amine compound is used in the manufacturing process of urethane polymers. In addition, the urethane polymers prepared by using the inventive amine compound are also almost free from any odor sometimes unavoidable with conventional amines to give unpleasantness to the user. Moreover, the amine compound of the invention has good miscibility with water or a polyol compound so that the manufacturing process of urethane polymers can be performed with good efficiency even when the amine catalyst is to be used as a solution in water or in the polyol compound.

Examples of the amine compound in conformity with the general formula (I) include: tris[2-(4-morpholino)ethyl] amine; tris[2-(2,6-dimethyl-4-morpholine)ethyl] amine; tris[2(2,6-diethyl-4-morpholino)ethyl] amine; tris[2-(2-methyl-4-morpholino)ethyl] amine; tris[2-(2-ethyl-4-morpholino)ethyl] amine; bis[2-(2,6-dimethyl-4-morpholino)ethyl]-[2-(4-morpholino)ethyl] amino; bis[2-(2,6-dimethyl-4-morpholino)ethyl]-[2-(2,6-diethyl-4-morpholino)ethyl] amine; bis[2-(2,6-dimethyl-4-morpholino)ethyl]-[2-(2-methyl-4-morpholino)ethyl] amine; bis[2-(2,6-dimethyl-4-morpholino)ethyl]-[2-(2,6-diethyl-4-morpholino)ethyl] amine; bis[2-(2,6-diethyl-4-morpholino)ethyl]-[2-(4-morpholino)ethyl] amine; bis[2-(2,6-diethyl-4-morpholine)ethyl]-[2-(2,6-dimethyl-4-morpholino)ethyl] amino; bis[2-(2,6-diethyl-4-morpholino)ethyl]-[2-(2-methyl-4-morpholino)ethyl] amine; bis[2-(2,6-diethyl-4-morpholino)ethyl]-[2-(2-ethyl-4-morpholino)ethyl] amine; bis[2-(2-methyl-4-morpholino)ethyl]-[2-(4-morpholino)ethyl] amine; bis[2-(2-methyl-4-morpholino)ethyl]-[2-(2,6-dimethyl-4-morpholino)ethyl] amine; bis[2-(2-methyl-4-morpholino)ethyl]-[2-(2,6-diethyl-4-morpholino)ethyl] amine; bis[2-(2-methyl-4-morpholino)ethyl]-[2-(2-ethyl-4-morpholino)ethyl] amine; bis[2-(2-ethyl-4-morpholino)ethyl]-[2-(4-morpholino)ethyl] amine; bis[2-(2-ethyl-4-morpholino)ethyl]-[2-(2,6-dimethyl-4-morpholino)ethyl] amine; bis[2-(2-ethyl-4-morpholino)ethyl]-[2-(2,6-diethyl-4-morpholino)ethyl] amine; bis[2-(2-ethyl-4-morpholino)ethyl]-[2-(2-methyl-4-morpholino)ethyl] amine; 2-(2,6-dimeth-yl-4-morpholino)ethyl]-bis[2-(4-morpholino)ethyl] amine; 2-(2,6-diethyl-4-morpholino)ethyl]-bis[2-(4-morpholino)ethyl] amine; 2-(2-methyl-4-morpholino)ethyl]-bis[2-(4-morpholino)ethyl] amine; 2-(2-ethyl-4-morpholino)ethyl]-bis[2-(4-morpholino)ethyl] amine; bis[2-(2-methyl-4-morpholino)ethyl]-[2-(4-morpholino)ethyl] amine; and bis[2-(2-methyl-4-morpholino)ethyl]-[2-(2,6-diethyl-4-morpholino)ethyl] amine. Among the above named amine compounds, tris[2-(4-morpholino)ethyl] amine and tris[2-(2,6-dimeth-yl-4-morpholino)ethyl] amine are preferred as a catalyst for the urethane-forming reaction in respect of the high catalytic activity in addition to the easiness in the synthetic preparation.

The above named amine compounds of the invention can be in the form of a salt with an organic or inorganic acid and the amine salts also can be used as the catalyst for the urethane-forming reaction. Examples of the salt-forming organic acids include aliphatic carboxylic acids such as monobasic carboxylic acids, e.g., formic acid, acetic acid and caprylic acid, and polybasic carboxylic acids, e.g., succinic acid and adipic acid, aromatic carboxylic acids such as monobasic carboxylic acids, e.g., benzoic acid, and polybasic carboxylic acids, e.g., phthalic acid and trimellitic acid, phenolic compounds, e.g., phenol and cathechol, and sulfonic acids, e.g., p-toluene sulfonic acid and methane sulfonic acid. Examples of the salt-forming inorganic acids include carbonic acid, hydrochloric acid, sulfuric acid, phosphoric acid, nitric acid and the like.

The novel tertiary amine compound of the invention represented by the general formula (I) can be synthesized by heating a tertiary alkanol amine compound represented by the general formula (II) together with sulfuric acid at a temperature in the range from 130° to 280° C. or, preferably, from 150° to 180° C. for a length of time in the range from 2 to 10 hours to effect the ring-closing reaction by the intramolecular condensation between the alkanol groups. The amount of the sulfuric acid is in the range from 70 to 200 parts by weight or, preferably, 90 to 150 parts by weight per 100 parts by weight of the starting alkanol amine compound of the general formula (II). After completion of the ring-closing reaction, the reaction mixture is neutralized with a suitable alkali such as sodium hydroxide and, if necessary, subjected to phase separation and drying followed by distillation so that the inventive amine compound can be isolated in a good yield.

The alkanol amine compound of the general formula (II) used as a starting material in the preparation of the inventive amine compound can be prepared by the addition reaction of tris(2-aminoethyl) amine, which is availabe as a commercial product, with an alkylene oxide in an amount of 6 times by moles. The alkylene oxide used in the above mentioned addition reaction is selected from those having 2 to 4 carbon atoms in a molecule including ethylene oxide, propylene oxide and butylene oxide, which can be used either singly or as a combination of two kinds or more according to need. It is preferable to use ethylene oxide and/or propylene oxide. The above mentioned addition reaction of the alkylene oxide to tris(2-aminoethyl) amine can be performed according to a known procedure at a temperature in the range from 50° to 200° C. or, preferably, from 100° to 180° C.

The novel amine compound of the invention prepared in the above described manner or a salt thereof is useful as a catalyst for the urethane-forming reaction between a polyisocyanate compound and a multifunctional active hydrogen-containing compound.

Any of known polyisocyanate compounds can be used in the urethane-forming reaction using the inventive amine compound as the catalyst. Examples of usable polyisocyanate compounds include aromatic polyisocyanates such as tolylene diisocyanate and diphenyl methane diisocyanate and aliphatic polyisocyanates such as hexamethylene diisocyanate and isophorone diisocyanate as well as derivatives thereof modified with a partial carbodiimide, isocyanurate and the like. Also usable are prepolymers containing free isocyanate obtained by the partial reaction of the above named polyisocyanate compound and a multifunctional active hydrogen-containing compound. These polyisocyanate compounds can be used either singly or as a combination of two kinds or more according to need.

The multifunctional active hydrogen-containing compound as a counterpart of the polyisocyanate compound in the urethane-forming reaction includes water, low-molecular polyols, high-molecular polyols and polyamines and they can be used either singly or as a combination of two kinds or more according to need.

Any of known low-molecular polyol compounds can be used without particular limitations. Examples of the low-molecular polyol compound include amine-type low-molecular polyols such as triethanol amine and diethanol amine and low-molecular polyols containing no nitrogen atoms such as ethylene glycol, diethylene glycol, butane diol, trimethylol propane, glycerin and 1,4-bis(2-hydroxyethyl) phenylene ether and they can be used either singly or as a combination of two kinds or more.

Any of known high-molecular polyol compounds can be used without particular limitations. Examples of the high-molecular polyol compound include: polyether polyols as an adduct of an alkylene oxide, e.g., ethylene oxide and propylene oxide, to water, a low-molecular polyol, e.g., ethylene glycol, propylene glycol, glycerin, trimethylol propane, triethanol amine, pentaerithritol, sorbitol and sucrose, or a polyamine, e.g., ethylene diamine, diethylene triamine, tolylene diamine, xylylene diamine, piperazine, N-aminoalkyl piperazines, N,N-dimethylaminoalkyl amines and cyclohexylene diamine; polymeric polyols obtained by the reaction of a polyether polyol and an ethylenically unsaturated monomer, e.g., acrylonitrile, styrene, methyl methacrylate and butadiene (see, for example, U.S. Pat. No. 3,383,351); and polyester polyols obtained by the esterification reaction of a polybasic carboxylic acid, e.g., succinic acid, maleic acid, sebacic acid, adipic acid, fumaric acid, phthalic acid and dimer acid, and a low-molecular polyol compound mentioned above. These high-molecular polyol compounds can also be used either singly or as a combination of two kinds or more according to need.

Any of known polyamine compounds can be used as a class of the multifunctional active hydrogen-containing compound. Examples of the polyamine compound include tolylene diamine, xylylene diamine, diamino diphenyl methane and methylene bis-2-chloroaniline and they can be used either singly or as a combination of two kinds or more according to need.

The inventive amine compound or a salt thereof alone can be used as a catalyst in the preparation of a flexible, rigid or semiflexible polyurethane foam or polyurethane resin, optionally, in combination with a known catalyst. Examples of such a known catalyst include amine compounds such as 1,4-diazabicyclo-(2,2,2)octane, 1,3,5-tris(3-dimethylaminopropyl) hexahydro-s-triazine, N,N,N',N'-tetremethyl hexamethylene diamine, N,N,N-tris(dimethylaminopropyl) amine, N-methyl-N,N-bis(dimethylaminopropyl) amine, N-methyl dicyclohexyl amine, 1,2-dimethyl imidazole, 1,8-diazabicyclo(5,4,0)undecene-7 and the like. When these known amine compounds are used in combination with the inventive amine compound, the weight proportion of the inventive amine compound to the known amine compound should not be smaller than 1:10 or, preferably, should not be smaller than 1:4.

It is further optional that the inventive amine compound is used as a catalyst for the urethane-forming reaction in combination with a metallic compound such as stannous octoate, dibutyl tin dilaurate and tin mercaptide having catalytic activity. When these metallic compounds are used in combination with the inventive amine compound, the weight proportion of the inventive amine compound to the known metallic compound should not be smaller than 1:10 or, preferably, should not be smaller than 1:5.

It is of course optional that the reaction mixture for the preparation of a polyurethane foam or a polyurethane resin is admixed with various kinds of known additives such as surface active agents, blowing agents, fillers, coloring agents, antioxidants and the like to serve as a crosslinking agent, emulsifier, stabilizer or cell-conditioning agent.

The catalyst in the urethane-forming reaction, which can be performed according to a known procedure, is used in an amount in the range from 0.01 to 10 parts by weight per 100 parts by weight of the polyol compound in the preparation of a polyurethane foam and in the range from 0.01 to 5 parts by weight per 100 parts by weight of the urethane prepolymer in the preparation of a polyurethane resin.

In the following, examples are given to illustrate the inventive amine compound and the method for the preparation thereof as well as the application thereof as a catalyst for the preparation of a urethane polymer although the scope of the present invention is never limited thereto. In the examples given below, the infrared absorption spectrum (IR) of the amine compound was taken by the direct-contact method and the nuclear magnetic resonance absorption spectrum ($^1$H-NMR) of the compound was measured in deuterated chloroform CDCl$_3$. The total amine value of the compound was determined by the titrimetric method with hydrochloric acid. The term of "parts" in the following description always refers to "parts by weight".

EXAMPLE 1

Tris[2-(4-morpholino)ethyl] amine was prepared in the following manner. Thus, 146 g (1 mole) of tris(2-aminoethyl) amine were taken in an autoclave and, after purging the air inside with nitrogen, it was heated up to 130° C. While keeping the temperature of the amine compound in the autoclave at 125° to 130° C., 277 g (6.3 moles) of ethylene oxide were introduced into the autoclave under pressurization from a small gas cylinder to effect the addition reaction. After completion of the introduction of the above mentioned amount of ethylene oxide, the reaction mixture in the autoclave was heated to 150° C. and kept at this temperature for 1 hour followed by cooling down to 130° C. where unreacted ethylene oxide was discharged out of the autoclave before cooling to room temperature. In this manner, 410 g of a viscous alkanol amine compound having a total amine value of 410 mg KOH/g were obtained as an addition product of ethylene oxide in a yield of 97% of the theoretical value assuming that the product was tris[2-di(2-hydroxyethyl)aminoethyl]amine.

Figure 2:
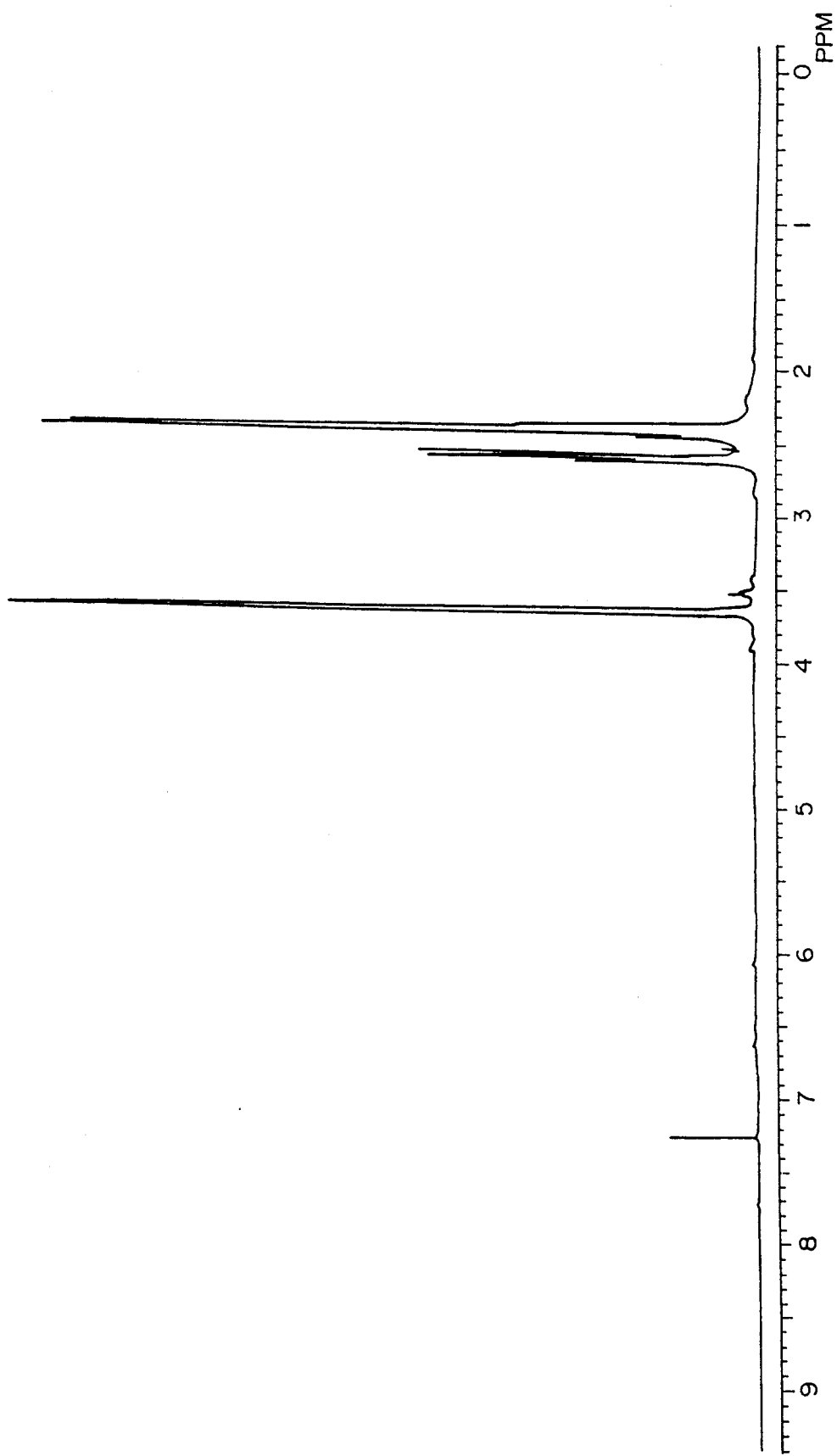

A 205 g portion of the thus obtained alkanol amine compound was added to 250 g of sulfuric acid under agitation to form a reaction mixture which was agitated for 6 hours at 170° C. followed by cooling to 60° C. In the course of cooling, 500 g of a 48% by weight aqueous solution of sodium hydroxide were added to the reaction mixture to neutralize the sulfuric acid. The reaction mixture cooled to room temperature was freed from precipitates of a salt by filtration and the filtrate was subjected to phase separation so as to discard the aqueous phase. The organic liquid obtained by the phase separation was subjected to distillation under reduced pressure to give 99 g of a fraction boiling at 200° to 210° C. under a pressure of 1 mmHg after discarding the preceding fractions of lower boiling points. An IR spectrum and a $^1$H-NMR spectrum of this product are shown in FIGS. 1 and 2, respectively. The total amine value of this product compound was 458 mg KOH/g which was in good coincidence with the theoretical value of 472 mg KOH/g assuming that the product compound was tris[2-(4-morpholino)ethyl] amine which was also supported by the results of the IR and $^1$H-NMR spectra. The above mentioned yield of the product corresponds to 55% of the theoretical value.

EXAMPLE 2

Tris[2-(2,6-dimethyl-4-morpholino)ethyl] amine was prepared in the following manner. Thus, 146 g (1 mole) of tris(2-aminoethyl) amine and 365 g (6.3 moles) of propylene oxide were reacted at 100° to 110° C. for 5 hours in an autoclave and the reaction mixture was then kept at 150° C. for 1 hour. Thereafter, the reaction mixture was cooled to 130° C. where the unreacted propylene oxide was discharged by releasing the autoclave before cooling to room temperature. In this manner, a viscous product having a total amine value of 330 mg KOH/g, which could be assumed to be tris[N,N-di(2-hydroxypropyl)aminoethyl] amine as an adduct of propylene oxide to the starting amine compound.

Figure 3:
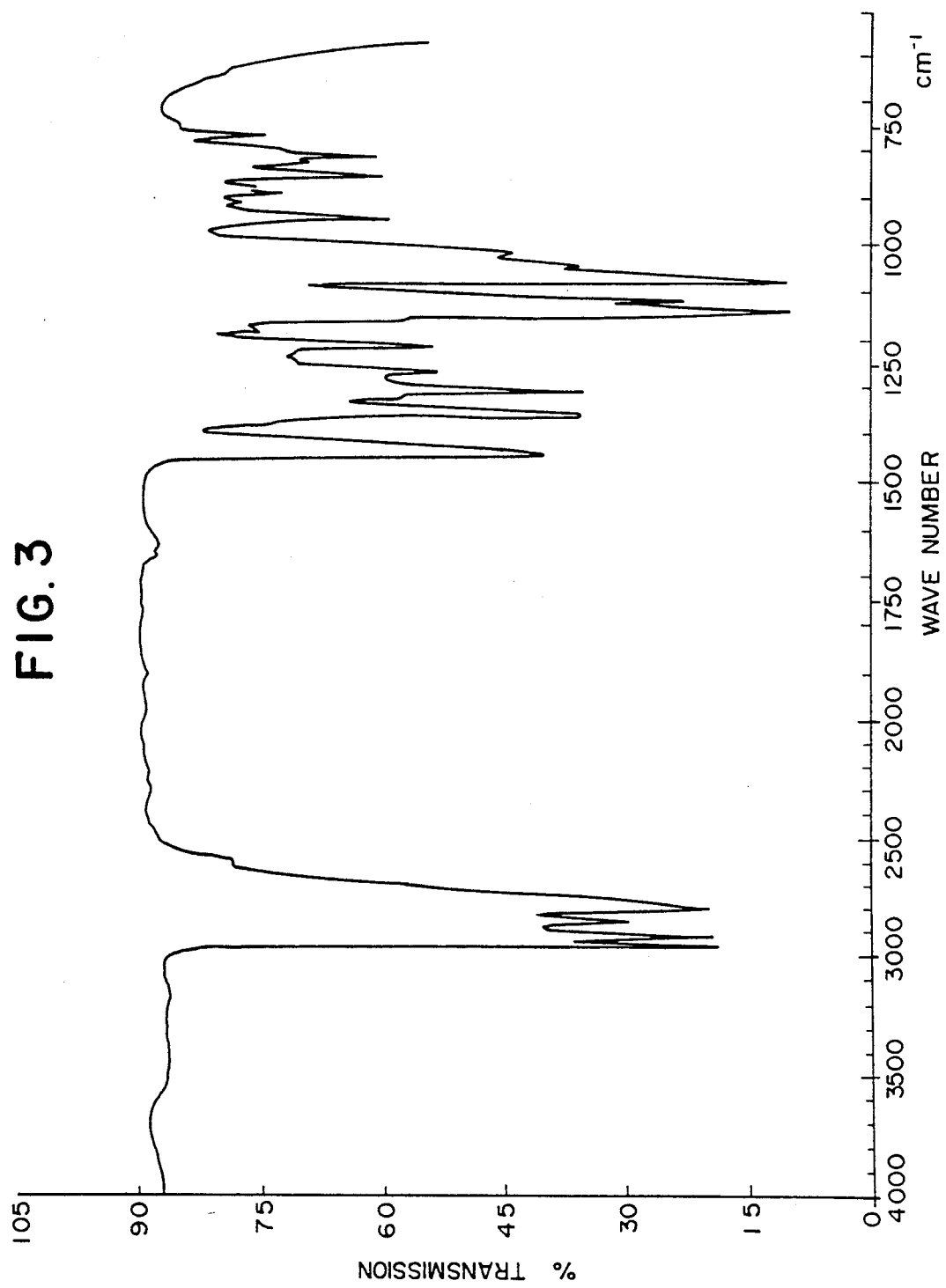
FIGS. 3 and 4 show an infrared absorption spectrum and a nuclear magnetic resonance absorption spectrum, respectively, of the inventive amine compound synthesized in Example 2.
Figure 4:
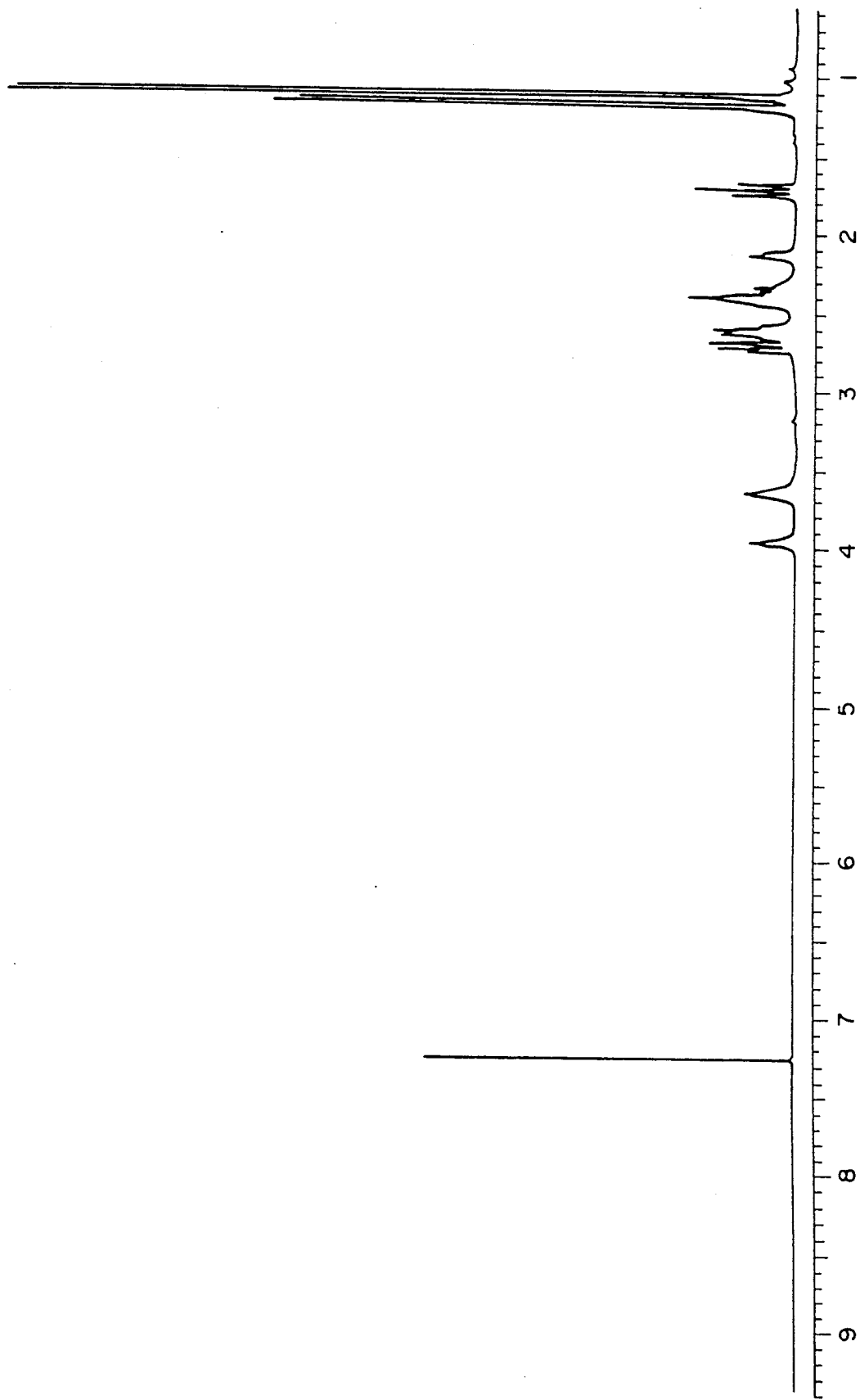

A 198 g portion of the thus obtained alkanol amine compound was added to 188 g of sulfuric acid under agitation to form a reaction mixture which was agitated for 5 hours at 170° to 180° C. followed by cooling to 60° C. In the course of cooling, 416 g of a 48% by weight aqueous solution of sodium hydroxide were added to the reaction mixture to neutralize the sulfuric acid. The reaction mixture cooled to room temperature was freed from precipitates of a salt by filtration and the filtrate was subjected to phase separation so as to discard the aqueous phase. The organic liquid obtained by the phase separation was subjected to distillation under reduced pressure to give 125 g of a fraction boiling at 204° to 212° C. under a pressure of 0.5 to 1 mmHg after discarding the preceding fractions of lower boiling points. An IR spectrum and a $^1$H-NMR spectrum of this product are shown in FIGS. 3 and 4, respectively. The total amine value of this product compound was 375 mg KOH/g which was in good coincidence with the theoretical value of 382 mg KOH/g assuming that the product compound was tris[2-(2,6-dimethyl-4-morpholino)ethyl] amine which was also supported by the results of the IR and $^1$H-NMR spectra. The above mentioned yield of the product corresponds to 71% of the theoretical value.

EXAMPLE 3

The amine compound prepared in the above described Example 1 was subjected to the test for the activity as a catalyst in the urethane-forming reaction to give a rigid polyurethane foam according to a standard formulation. The materials included in the formulation were:

100 parts of a sugar-based polyol having an OH value of about 440 (SU-464, a product by Mitsui Toatsu Chemicals, Inc.);
20 parts of an amine-based polyol having an OH value of about 450 (ED-450, a product by the same company as above);
1.5 parts of water;
1.5 parts of a silicone-based foam-conditioning agent (SH-193, a product by Toray Silicone Co.); 34 parts of Freon-11;
a varied amount of the amine compound; and
a crude methylene diisocyanate (MDI-CR200, a product by Mitsui Toatsu Chemicals, Inc.) in an amount corresponding to 110 NCO index.

Taking 50 g of the polyol compounds, the urethane mixture was subjected to foaming at 20° C. according to a conventional procedure in a foaming box having dimensions of 15 cm by 12 cm wide and 20 cm depth to determine the processing times in seconds including the cream time, referred to as the "ct" hereinbelow, gel time, referred to as the "gt" hereinbelow, and tack-free time, referred to as the "tft" hereinbelow, to give the results shown in Table 1 below.

TABLE 1

| Amine compound taken, parts | ct | gt | tft |
|---|---|---|---|
| 2 | 23 | 280 | 455 |
| 4 | 19 | 210 | 320 |
| 6 | 12 | 175 | 235 |

EXAMPLE 4

A foaming test for the preparation of a flexible polyurethane foam was undertaken by using the amine compound prepared in Example 1 as the catalyst. Thus, 100 parts of a polyol having an average molecular weight of about 3000 and a hydroxyl value of 56 mg KOH/g, which was an addition product of propylene oxide to glycerin (Sannix GP-3000, a product by Sanyo Chemical Industries, Ltd.), 4.5 parts of water, 2 parts of a silicone-based foam conditioning agent (L-520, a product by Nippon Unicar Co.), 0.2 part of the amine compound prepared in Example 1 and 0.34 part of stannous octoate were mixed together and the mixture was admixed with 54.8 parts of tolylene diisocyanate (TDI-80, a product by Mitsui Toatsu Chemicals, Inc.) and vigorously agitated for 7 seconds using a high-speed stirrer followed by transfer of the mixture into a carton box so that a flexible polyurethane foam having excellent properties could be obtained with a rise time of 96 seconds.

What is claimed is:

1. A morpholino-substituted tertiary amine compound represented by the general formula

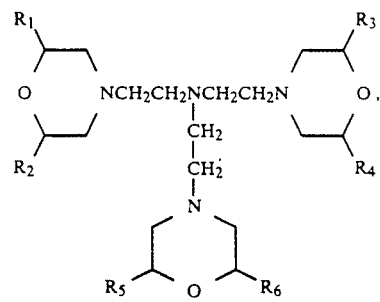

in which $R_1$, $R_2$, $R_3$, $R_4$, $R_5$ and $R_6$ are, each independently from the others, a hydrogen atom, methyl group or ethyl group, in the form of a free amine or a salt thereof.

2. Tris[2-(4-morpholino)ethyl]amine.

3. Tris[2-(2,6-dimethyl-4-morpholino)ethyl]amine.

* * * * *